(12) United States Patent
Judkins

(10) Patent No.: US 8,843,206 B2
(45) Date of Patent: Sep. 23, 2014

(54) TELEMETRY ANTENNAS FOR MEDICAL DEVICES AND MEDICAL DEVICES INCLUDING TELEMETRY ANTENNAS

(75) Inventor: James G. Judkins, Campbell, CA (US)

(73) Assignee: Spinal Modulation, Inc., Menlo Park, CA (US)

( * ) Notice: Subject to any disclaimer, the term of this patent is extended or adjusted under 35 U.S.C. 154(b) by 0 days.

(21) Appl. No.: 13/399,693

(22) Filed: Feb. 17, 2012

(65) Prior Publication Data

US 2012/0265272 A1 Oct. 18, 2012

Related U.S. Application Data

(60) Provisional application No. 61/475,197, filed on Apr. 13, 2011.

(51) Int. Cl.
*A61N 1/00* (2006.01)

(52) U.S. Cl.
USPC .......................................................... 607/60

(58) Field of Classification Search
USPC .................................................. 607/60, 2
See application file for complete search history.

(56) References Cited

U.S. PATENT DOCUMENTS

| | | | |
|---|---|---|---|
| 6,239,760 B1 | 5/2001 | Van Voorhies | |
| 6,240,317 B1 | 5/2001 | Villaseca et al. | |
| 6,392,610 B1 | 5/2002 | Braun et al. | |
| 6,505,072 B1 | 1/2003 | Linder et al. | |
| 6,708,065 B2 | 3/2004 | Von Arx et al. | |
| 6,931,284 B2 | 8/2005 | Engmark et al. | |
| 6,987,494 B2 | 1/2006 | Keren | |
| 7,049,818 B2 | 5/2006 | Rinneberg et al. | |
| 7,317,946 B2 | 1/2008 | Twetan et al. | |
| 7,483,752 B2 | 1/2009 | Von arx et al. | |
| 7,586,463 B1 | 9/2009 | Katz | |
| 7,720,544 B2 | 5/2010 | Christman et al. | |
| 7,729,766 B2 | 6/2010 | Toy et al. | |
| 2005/0088352 A1 | 4/2005 | Parsche | |
| 2005/0134520 A1 | 6/2005 | Rawat et al. | |
| 2005/0149139 A1 | 7/2005 | Plicchi et al. | |
| 2005/0182451 A1 | 8/2005 | Griffen et al. | |
| 2005/0267550 A1 | 12/2005 | Hess et al. | |
| 2006/0224206 A1 | 10/2006 | Dublin et al. | |
| 2008/0021522 A1* | 1/2008 | Verhoef et al. | 607/60 |
| 2009/0270948 A1 | 10/2009 | Nghiem et al. | |
| 2010/0109966 A1 | 5/2010 | Mateychuk et al. | |
| 2010/0137938 A1 | 6/2010 | Kishawi et al. | |

OTHER PUBLICATIONS

International Search Report and Written Opinion dated Jul. 27, 2012, in PCT/US2012/032194.
Bancroft, R., "Fundamental Dimension Limits of Antennas: Ensuring Proper Antenna Dimensions in Mobile Device Designs," Ceturion Wireless Technologies, http://www.xertex.com/home/pdf/wp_dimension_limits.pdf, date unknown, (accessed May 9, 2011), pp. 1-14.

* cited by examiner

*Primary Examiner* — Christopher D Koharski
*Assistant Examiner* — Nadia Ahmad
(74) *Attorney, Agent, or Firm* — Vierra Magen Marcus LLP

(57) ABSTRACT

In an embodiment, an antenna for a medical device, e.g., an implantable medical device (IMD), comprises an electrically conductive wire that spirals to form a three-dimensional shape of a rectangular cuboid. In another embodiment, the antenna comprises an electrically conductive wire that spirals to form a three-dimensional shape of an elliptical cylinder, an oval cylinder, an elongated pentagonal prism, an elongated hexagonal prism, or some other shape where the longitudinal diameter of the antenna is greater than the lateral diameter of the antenna. The antennas are sized to fit within a portion of a header of the medical device. Such antennas are designed to provide increased antenna gain and antenna bandwidth.

32 Claims, 13 Drawing Sheets

(top view)

(front view)

(side view)

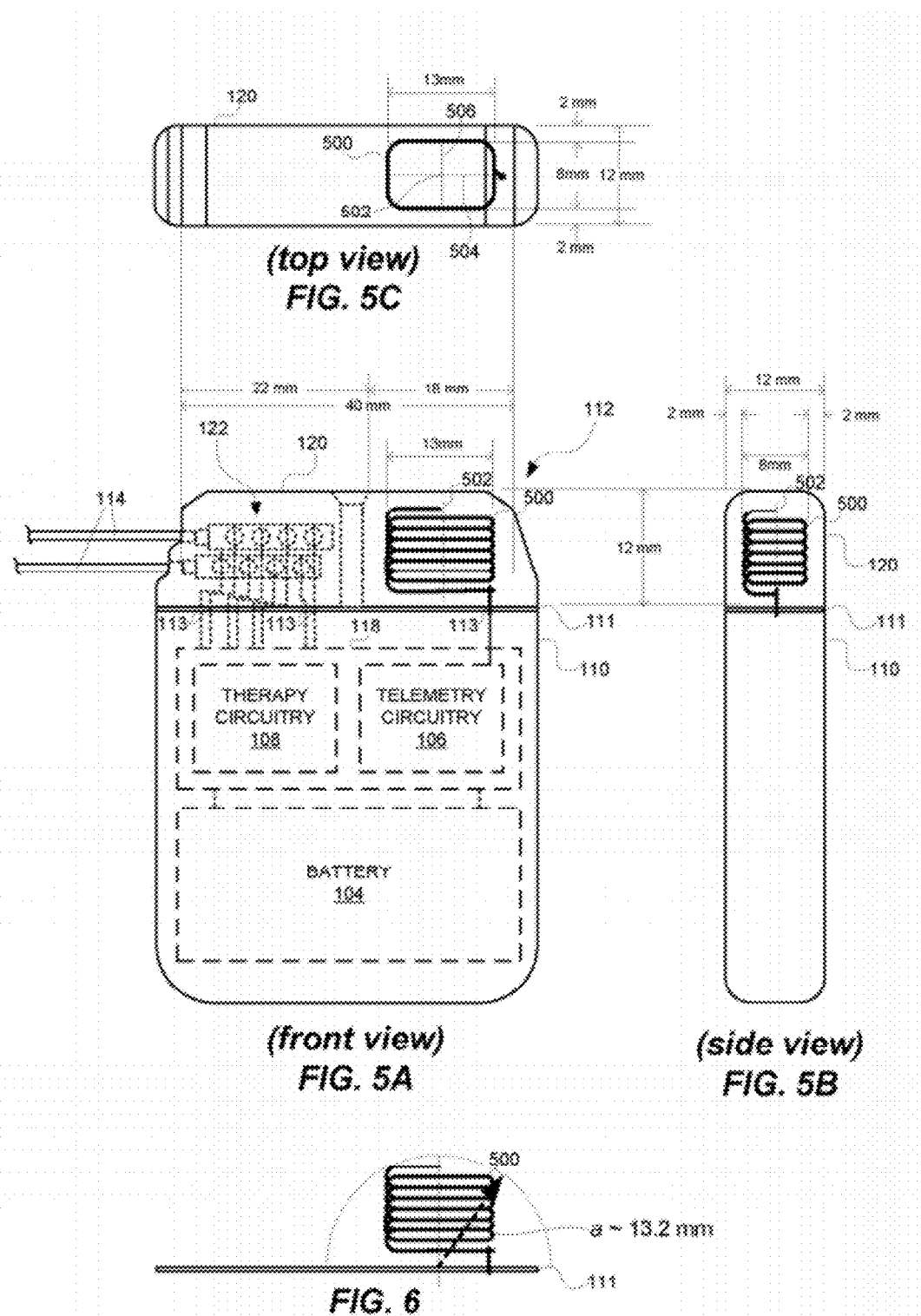

(perspective view)

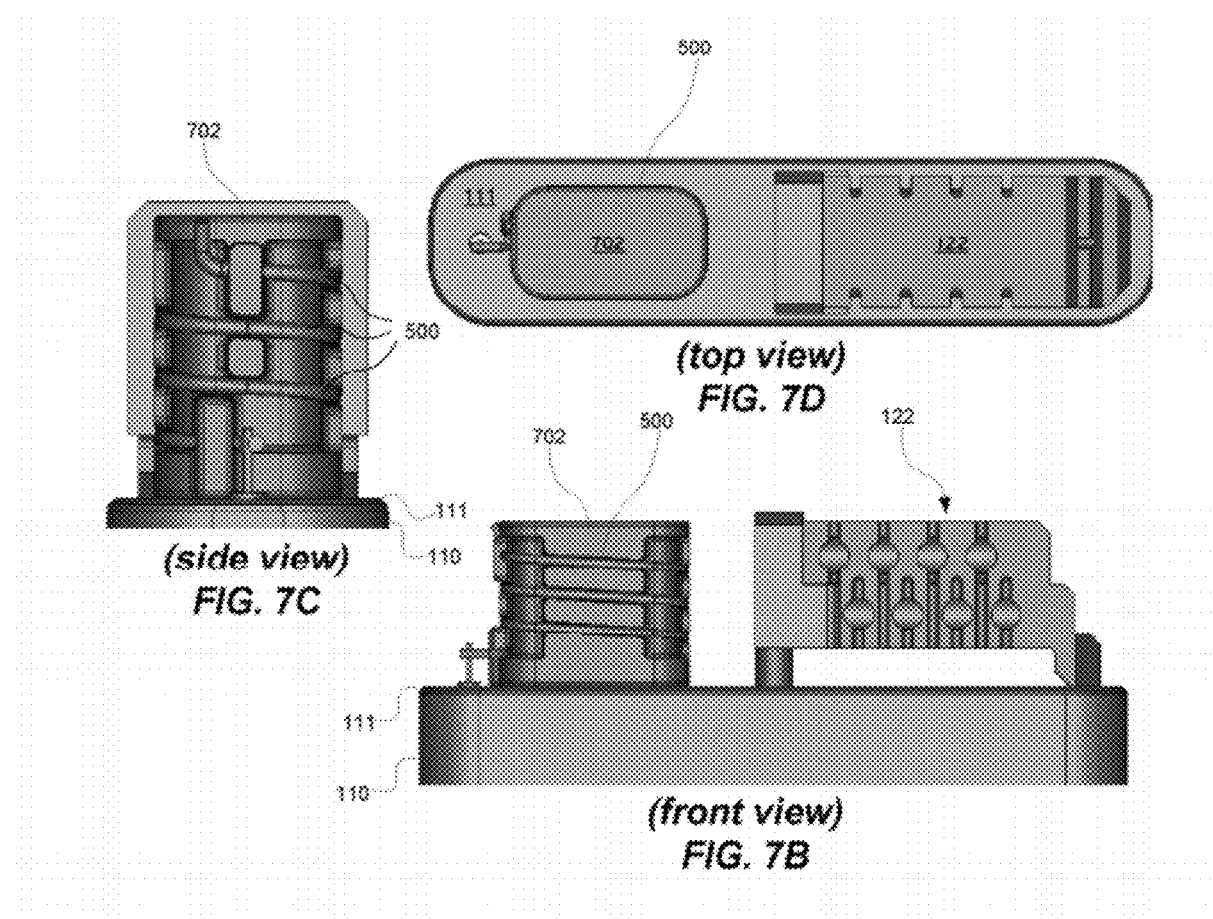

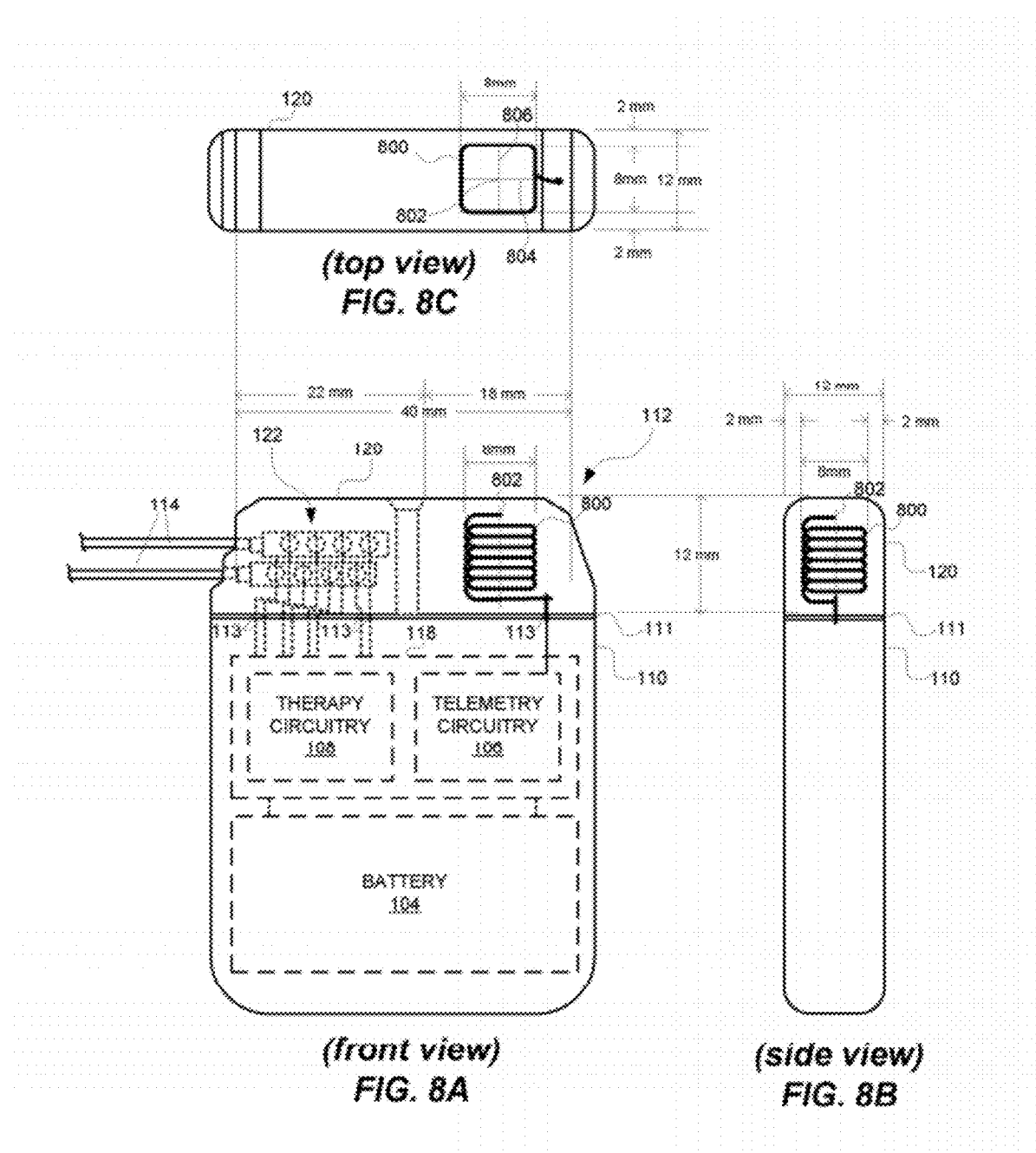

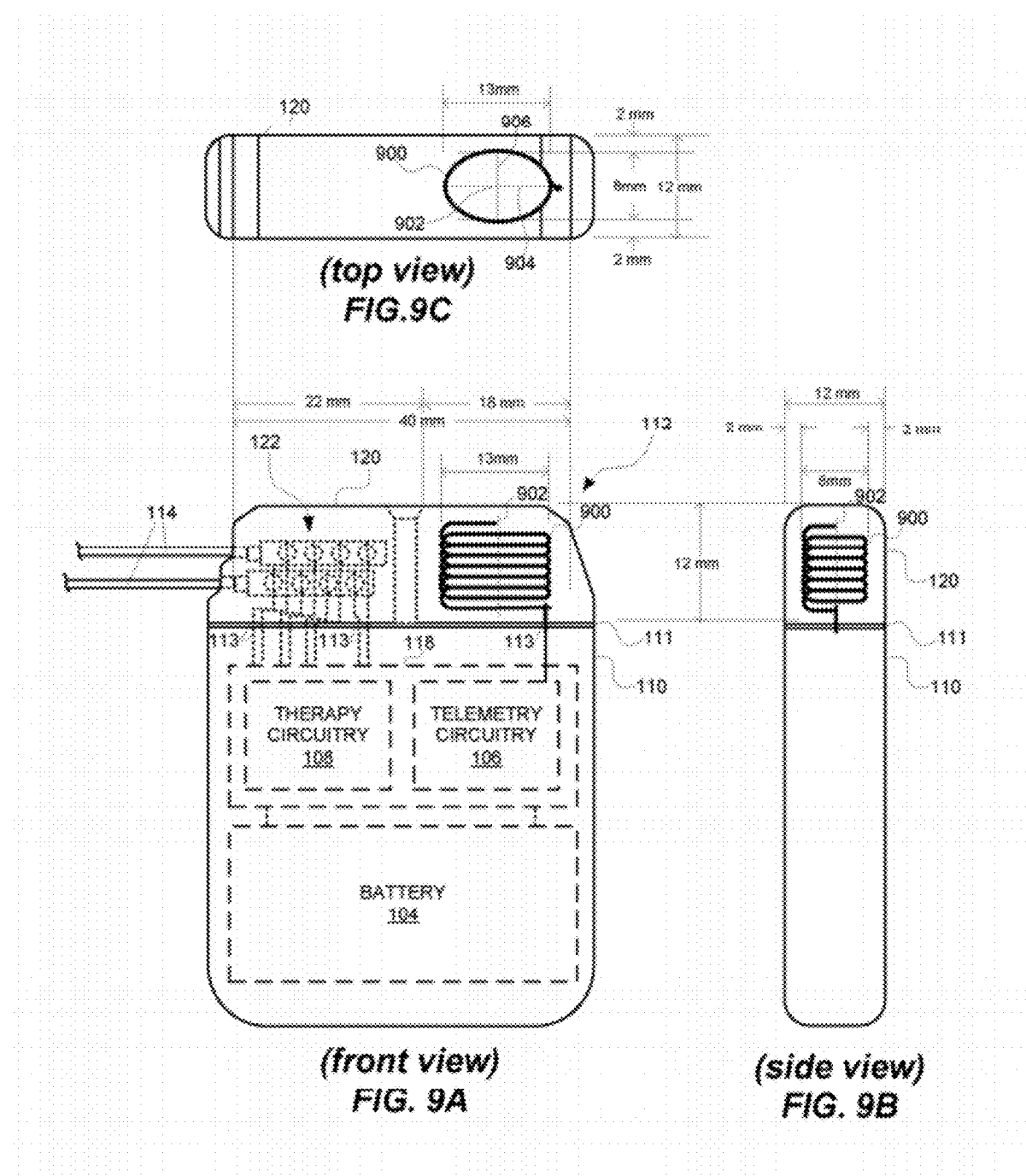

(top view)

(top view)

US 8,843,206 B2

TELEMETRY ANTENNAS FOR MEDICAL DEVICES AND MEDICAL DEVICES INCLUDING TELEMETRY ANTENNAS

PRIORITY CLAIM

This application claims priority under 35 U.S.C. 119(e) to U.S. Provisional Patent Application No. 61/475,197, filed Apr. 13, 2011, which is incorporated herein by reference.

FIELD OF THE INVENTION

Embodiments of the present invention generally relate to antennas for enabling medical devices to wireless communicate with base stations, medical devices including such antennas, and related methods, devices and systems.

BACKGROUND OF THE INVENTION

A medical device (MD) can be implanted in a patient for various different purposes, including, but not limited to, treating physiologic conditions, monitoring physiological conditions, treating neurological conditions, monitoring neurological conditions, diagnosing diseases, treating diseases, or restoring functions of organs or tissues. Where the MD is implanted, it is often referred to as an implantable medical device (IMD). Examples of IMDs include, but are not limited to, implantable neurostimulators, implantable cardiac rhythm management devices (e.g., implantable cardioverter defibrillators and pacemakers) and drug delivery devices. Because such a device may be implanted in a patient, the size of the device is inherently constrained. For this and other reasons, an IMD may depend on an external (i.e., non-implanted) system, generically referred to as a base station (BS), to perform certain functions. Such a non-implanted BS can be a patient programmer, a clinician programmer or a remote monitoring device, but is not limited thereto.

An implantable neurostimulator (INS) is an IMD that performs neurostimulation, which has become an accepted treatment for patients with chronic pain in their back and/or limbs who have not found pain relief from other treatments. In general, neurostimulation involves applying an electrical current to nerve tissue in the pathway of the chronic pain. This creates a sensation that blocks the brain's ability to sense the previously perceived pain. There are two conventional forms of electrical stimulation commonly used to treat chronic pain: Spinal Cord Stimulation (SCS) and Peripheral Nerve Field Stimulation (PNFS). In SCS, electrical leads are placed along the spinal cord. A programmable INS is typically implanted in the upper buttock or abdomen (under the skin) and emits electrical currents to the spinal cord via electrodes of the leads. Peripheral nerve field stimulation is similar to spinal cord stimulation, however peripheral nerve field stimulation involves placing the leads just under the skin in an area near to the peripheral nerves involved in pain.

Leads are often attached to an IMD, such as an INS, to deliver electrical stimulation via electrodes of the leads. An IMD often includes a hermetically sealed device housing within which is located electronic circuitry used for generating and controlling the electrical stimulation, and a header which is used to connect the leads to the IMD. The header is often molded from a relatively hard, dielectric, non-conductive polymer and typically has a thickness approximating the thickness of the device housing. The header typically includes a mounting surface that conforms to and is mechanically affixed to a mating sidewall surface of the device housing.

Wireless communication between an IMD and an external BS is often referred to as telemetry. Examples of specific telemetry functions include, but are not limited to, programming or instructing the IMD to perform certain therapeutic tasks and/or adjust certain therapeutic parameters, downloading firmware upgrades to the IMD, uploading operational status information (e.g., battery and/or impedance measurements) from the IMD, and uploading data stored within the IMD. A useful type of wireless communication is radio frequency (RF) communication since it does not require that the BS and the IMD be very close to one another. Rather, with RF communication the BS and the IMD can be many feet apart while still allowing for reliable communication.

A non-implanted BS and an IMD, such as an INS, can communicate using the Medical Implant Communication Service (MICS) standard, which was defined by the U.S. Federal Communications Commission (FCC) and European Telecommunications Standards Institute (ETSI). The MICS standard uses the RF band between 402 and 405 MHz to provide for bi-directional radio communication with IMDs, such as an INS. The RF band between 402 and 405 MHz can be broken down into multiple channels, e.g., into ten 300 kHz wide channels, but not limited thereto. In 2009 the FCC began referring to the RF band between 402 and 405 MHz as being part of the 401 to 406 MHz Medical Device Radiocommunications (MedRadio) Service band. Accordingly, for the remainder of this description, the RF band between 402 and 405 MHz will be referred to as the MICS/MedRadio band, and the communication standards relating to the MICS/MedRadio band will be referred to as the MICS/MedRadio communication standards. The use of other frequencies, e.g., in the range from 300 MHz through 1 GHz, but not limited thereto, are also possible. Further possible frequencies that can be used include industrial, scientific and medical (ISM) radio bands, such as, but not limited to, the 2.45 GHz and the 5.8 GHz bands, as well as much lower frequency bands.

An IMD, such as an INS, includes an antenna for use in receiving signals from a BS and transmitting signals to the BS. The antenna can be, for example, located within the hermetic device housing of the IMD, or within the header of the IMD. A benefit of locating the antenna within the header (as opposed to within the hermetic device housing) is that the antenna is generally isolated from electronic circuitry of the IMD, and thus, is generally not inadvertently affected by the electronic circuitry. Another reason to not locate an antenna within the hermetic device housing is that the sealed metal housing can prevent the antenna from radiating, i.e., the metal housing can shield the antenna. However, a challenge with locating the antenna within the header is that the header is small, and a relatively large portion of the header is already devoted to providing mechanical and electrical connections to the proximal ends of one or more therapy leads.

FIG. 1 illustrates an exemplary IMD 112 that includes a hermetically sealed device housing 110, which is typically made of medical grade metal. Contained within the housing 110 is electronic circuitry 118 used for generating and controlling the electrical stimulation, and a header 120 which is used to interconnect leads 114 to the IMD 112. The electronic circuitry 118 is shown as including therapy circuitry 108 and telemetry circuitry 106. The housing 110 is also shown as containing a battery 104 that is used to power the electronic circuitry 118.

A header 120, which is typically made of a medical grade polymer or other plastic, is mechanically affixed to a mating surface 111 of the device housing 110. As shown in FIG. 1, a portion 122 of the header 120 includes connectors (e.g., bores or sockets) that accept proximal ends of the leads 114 to thereby mechanically connect the leads to the header 120. Electrical conductors, e.g., wires and/or conductive traces, extend from the header 120 through feed-through openings 113 in the mating surface 111 of the device housing 110 to thereby electrically connect the leads 114, and the electrodes thereon, to the therapy circuitry 108.

As disclosed in U.S. Pat. No. 6,708,065 to Von Arx et al. (the '065 patent), a helical antenna can be embedded in the header. The 065' patent explains that two common types of antennas are wire dipole and monopole antennas. If a substantial portion of the RF energy delivered to the antenna is to be emitted as far-field radiation, the length of the antenna should not be very much shorter than one-quarter of the wavelength of the RF carrier signal provided by the RF transmitter. For implantable medical device applications, carrier frequencies between 300 MHz and 1 GHz are most desirable. For example, the carrier signal can be 1 GHz, which corresponds to a wavelength of approximately 30 cm. For a 30 cm wavelength, a half-wavelength dipole antenna would optimally be approximately 15 cm (i.e., 150 mm) long, and a quarter-wavelength monopole antenna would optimally have a length of approximately 7.5 cm (i.e., 75 mm) with the housing serving as a ground plane. Depending upon the size of the implantable device, it may not be possible or convenient to embed a straight wire antenna in a compartment of the device. For reasons of patient comfort, however, it is desirable for an implanted device to be as small as possible, and this constrains the length of the antenna that can be used if it is to be embedded in a compartment of the device.

The '065 patent explains that it employs a helical antenna to transmit and receive RF signals. The '065 patent also explains that its helical antenna is formed by helically coiling a length of wire or other conductor along a particular axis. If the circumference of the individual helices is small in comparison to the wavelength of the driving or received signal, the radiation pattern of the helical antenna is approximately the same as either a dipole antenna or a monopole antenna if a ground plane is present. A helical dipole or monopole antenna may be formed by coiling a length of wire corresponding to just over one-half wavelength or one-quarter wavelength of the carrier frequency. Owing to the coiling of the wire, the resulting helical antenna is physically shorter than the monopole or dipole antenna formed from the straight piece of wire. The effective electrical length of a helical antenna, however, is even longer than that owing to the added inductance of the coil and turn-to-turn capacitance which reduces the resonance frequency from that of the corresponding straight wire antenna. A helical antenna thus provides a shortened, space-saving monopole or dipole antenna that behaves electrically like a much longer antenna.

FIGS. 2A, 2B and 2C illustrate, respectively, how the '065 patent (in FIGS. 1A, 1B and 1C of the '065 patent) teaches locating and positioning a helical antenna 200 within the header 120. In FIG. 2A (which is similar to FIG. 1A of the '065 patent), the helical antenna 200 is positioned roughly parallel to the mating surface 111 of the device housing 110. In FIG. 2B (which is similar to FIG. 1B of the '065 patent), the helical antenna 200 is positioned perpendicular to the surface of the device housing 110. In FIG. 2C (which is similar to FIG. 1C of the '065 patent), the helical antenna 200 is helically wound around one of the bores into which a proximal end of a therapy lead inserts.

A helical antenna (e.g., 200), such as the antenna disclosed in the '065 patent, is an antenna having the shape of a helix. A helix is a smooth curve in three-dimensional space characterized by the fact that the tangent line at any point makes a constant angle with a fixed line called the axis. Another way of explaining a helix is the curve formed by a straight line drawn on a plane when that plane is wrapped around a right circular cylinder.

The '065 patent does not discuss whether or how the diameter or radius of a helical antenna affects performance of the antenna. Rather, the '065 patent only suggests how to select a length of a helical antenna. Further, from FIGS. 1A-1C of the '065 patent, the diameter and radius of the helical antenna shown therein appear to be small compared to the relative space available for locating the antenna within the header of the exemplary implantable device shown therein.

U.S. Pat. No. 6,505,072 to Linder et al. (the '072 patent), in FIG. 3 of the '072 patent, also discloses that a helical antenna can be disposed in the header of an IMD. However, the '072 patent also does not discuss whether or how the diameter or radius of a helical antenna affects performance of the antenna. Further, from FIG. 3 of the '072 patent, the diameter and radius of the helical antenna shown therein appears to be small compared to the relative space available for locating the antenna within the header of the exemplary implantable device shown therein.

BRIEF SUMMARY OF THE INVENTION

Specific embodiments of the present invention are directed to antennas for enabling medical devices to wireless communicate with base stations, medical devices including such antennas, and related methods, devices and systems.

In accordance with an embodiment of the present invention, a medical device includes a housing and a header that is mechanically affixed to a mating surface of the housing. Within the header is/are one or more connectors that is/are configured to receive a proximal end of one or more leads. A telemetry antenna is also located within the header. The medical device can be, e.g., an implantable medical device such as, but not limited to, an implantable neurostimulator. Additionally, the medical device includes telemetry circuitry within the housing, wherein the antenna is electrically connected to the telemetry circuitry by a conductor that extends from the antenna through a feed-through opening in the mating surface of the housing. In accordance with an embodiment, the medical device also includes therapy circuitry, within the housing, electrically connected to the one or more connectors within the header by one or more conductors that extend from the one or more connectors through one or more further feed-through openings in the mating surface of the housing. The therapy circuitry is configured to control stimulation that is deliverable via electrodes of one or more leads connected to the one or more connectors within the header. At least a portion of the housing is electrically conductive and acts as a ground plane for the antenna, with the mating surface of the housing being a portion of the ground plane that is closest to the antenna.

Since the connector(s) occupy a portion of the header, the portion of the header within which the antenna can be located is limited. In accordance with specific embodiments, the antenna is shaped to increase and attempt to maximize antenna gain and antenna bandwidth given the limited amount of space available for the antenna.

In accordance with an embodiment, the antenna spirals about a central axis and has a rectangular cuboid circumferential shape. In an embodiment, the central axis is perpendicular to the mating surface of the housing. A longitudinal diameter and a lateral diameter of the antenna cross one another at the central axis. In an embodiment the longitudinal diameter is greater than the lateral diameter. In another embodiment the longitudinal diameter is substantially equal to the lateral diameter, in which case the rectangular cuboid circumferential shape is a square cuboid circumferential shape.

An antenna gain and an antenna bandwidth of the antenna having the rectangular cuboid circumferential shape are greater than an antenna gain and an antenna bandwidth of a helical antenna having a right circular cylinder circumferential shape that could fit within the header. This is in part because a volume occupied by the antenna having the rectangular cuboid circumferential shape is greater than a volume that could be occupied by a helical antenna having a right circular cylinder circumferential shape that could fit within the header.

In accordance with alternative embodiments, the three-dimensional shape of the antenna can be an elliptic cylinder, an oval cylinder, an elongated pentagonal prism, an elongated hexagonal prism, or another three-dimensional shape that could fit within the header and has a larger volume than a helical antenna having a right circular cylinder circumferential shape (that could fit within the header). For a given amount of available space within a header of a medical device, these alternative embodiments can also be used to provide greater antenna gain and antenna bandwidth than could be obtained using a helical antenna having a right circular cylinder circumferential shape that could fit within the header. This is in part because a volume occupied by the antenna having a circumferential shape of an elliptical cylinder, an oval cylinder, an elongated pentagonal prism or an elongated hexagonal prism is greater than a volume that could be occupied by a helical antenna having a right circular cylinder circumferential shape that could fit within the header.

Embodiments of the present invention are also directed to antennas for medical devices, such as implantable medical devices. In accordance with an embodiment, an antenna for a medical device comprises an electrically conductive wire that spirals to form a three-dimensional shape of a rectangular cuboid. In one embodiment, a longitudinal diameter of the rectangular cuboid is greater than a lateral diameter of the rectangular cuboid. In another embodiment, a longitudinal diameter of the rectangular cuboid is substantially equal to a lateral diameter of the rectangular cuboid. In specific embodiments, the antenna is sized to fit within a portion of a header of an implantable medical device.

In accordance with certain embodiments, an antenna for a medical device comprises an electrically conductive wire that spirals to form a three-dimensional shape including a longitudinal diameter, a lateral diameter and a height, wherein the longitudinal diameter of the antenna is greater than the lateral diameter of the antenna. The three-dimensional shape of the antenna can be a rectangular cuboid. Alternatively, the three-dimensional shape of the antenna can be an elliptic or oval cylinder.

This summary is not intended to summarize all of the embodiments of the present invention. Further and alternative embodiments, and the features, aspects, and advantages of the embodiments of invention will become more apparent from the detailed description set forth below, the drawings and the claims.

BRIEF DESCRIPTION OF THE DRAWINGS

FIGS. 5A, 5B and 5C illustrate, respectively, a front view, side view and top view of an IMD including an antenna according to another embodiment of the present invention.

FIG. 6 illustrates how to draw a radius a of a sphere enclosing the maximum dimension of the antenna shown in FIGS. 5A-5C.

FIGS. 7B, 7C and 7D illustrate, respectively, a front view, side view and top view of the antenna whose perspective view is shown in FIG. 7A.

FIGS. 8A, 8B and 8C illustrate, respectively, a front view, side view and top view of an IMD including an antenna according to a further embodiment of the present invention.

FIGS. 9A, 9B and 9C illustrate, respectively, a front view, side view and top view of an IMD including an antenna according to still a further embodiment of the present invention.

DETAILED DESCRIPTION

Figure 1:
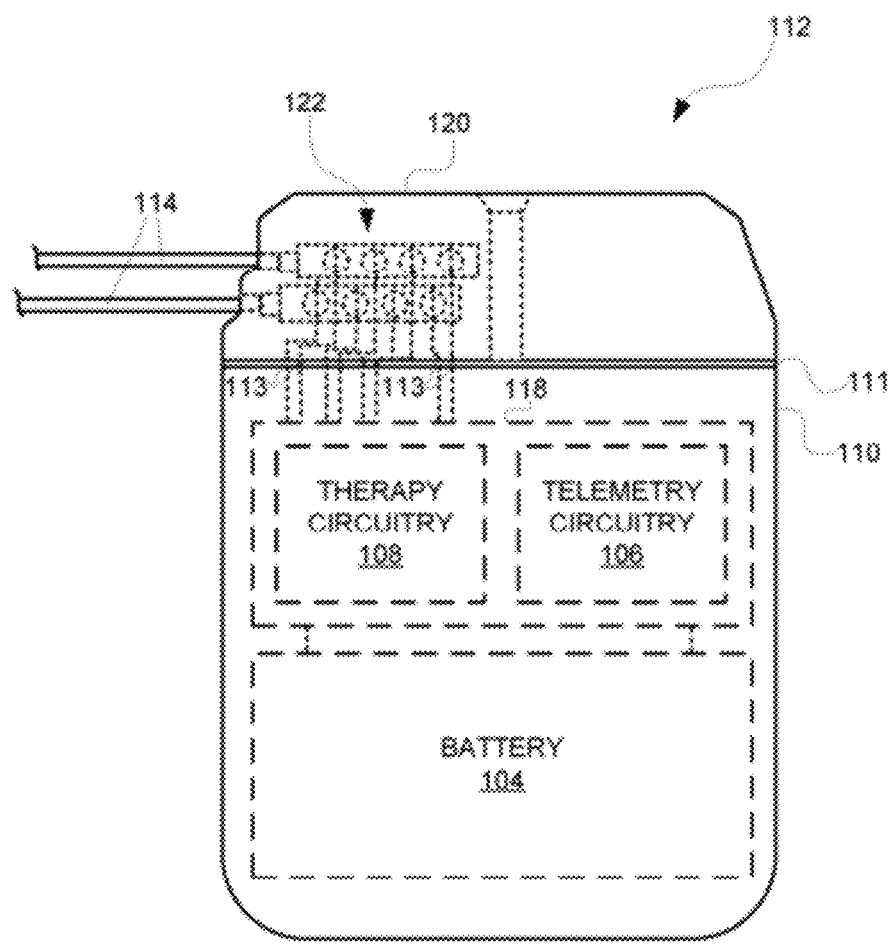
FIG. 1 illustrates an exemplary implantable medical device (IMD) including a hermetically sealed device housing and a header mechanically affixed to the device housing.
Figure 2A:
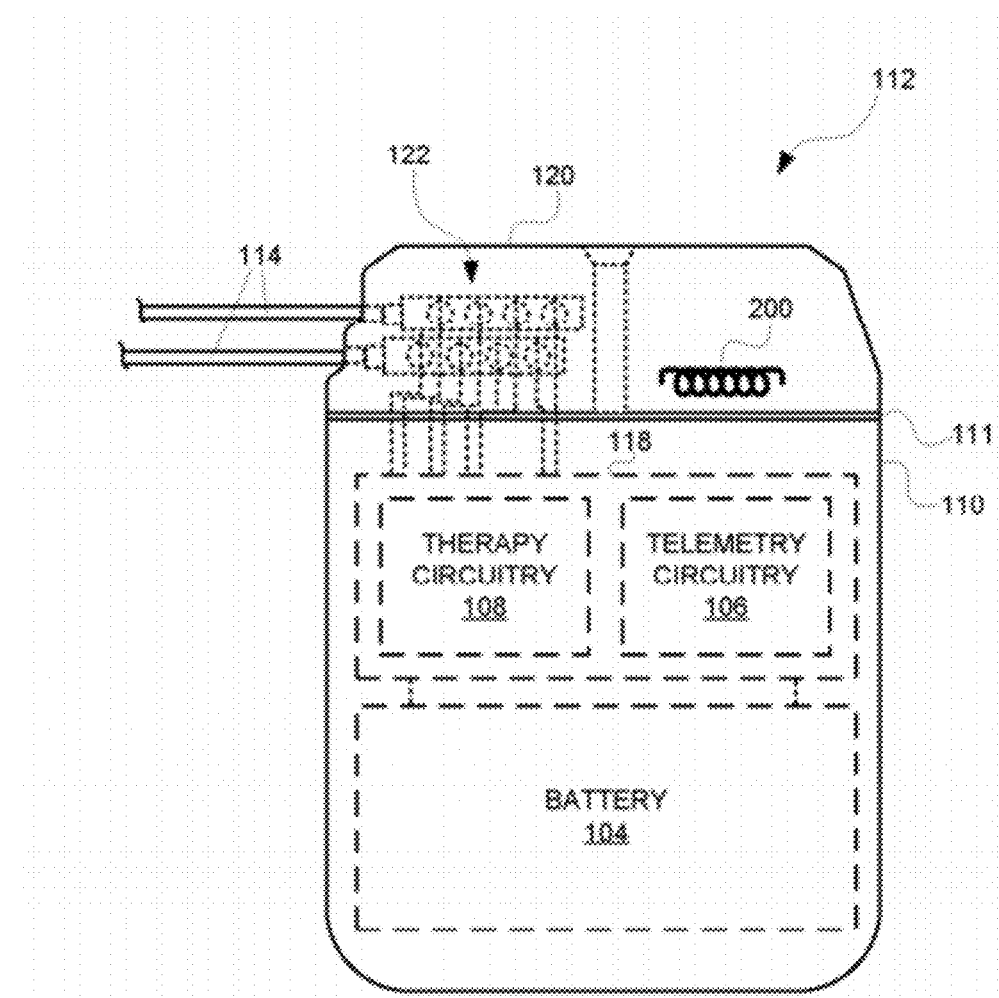
FIGS. 2A, 2B and 2C illustrate three exemplary manners in which a helical antenna can be located within the header of the exemplary IMD shown in FIG. 1.
Figure 2B:
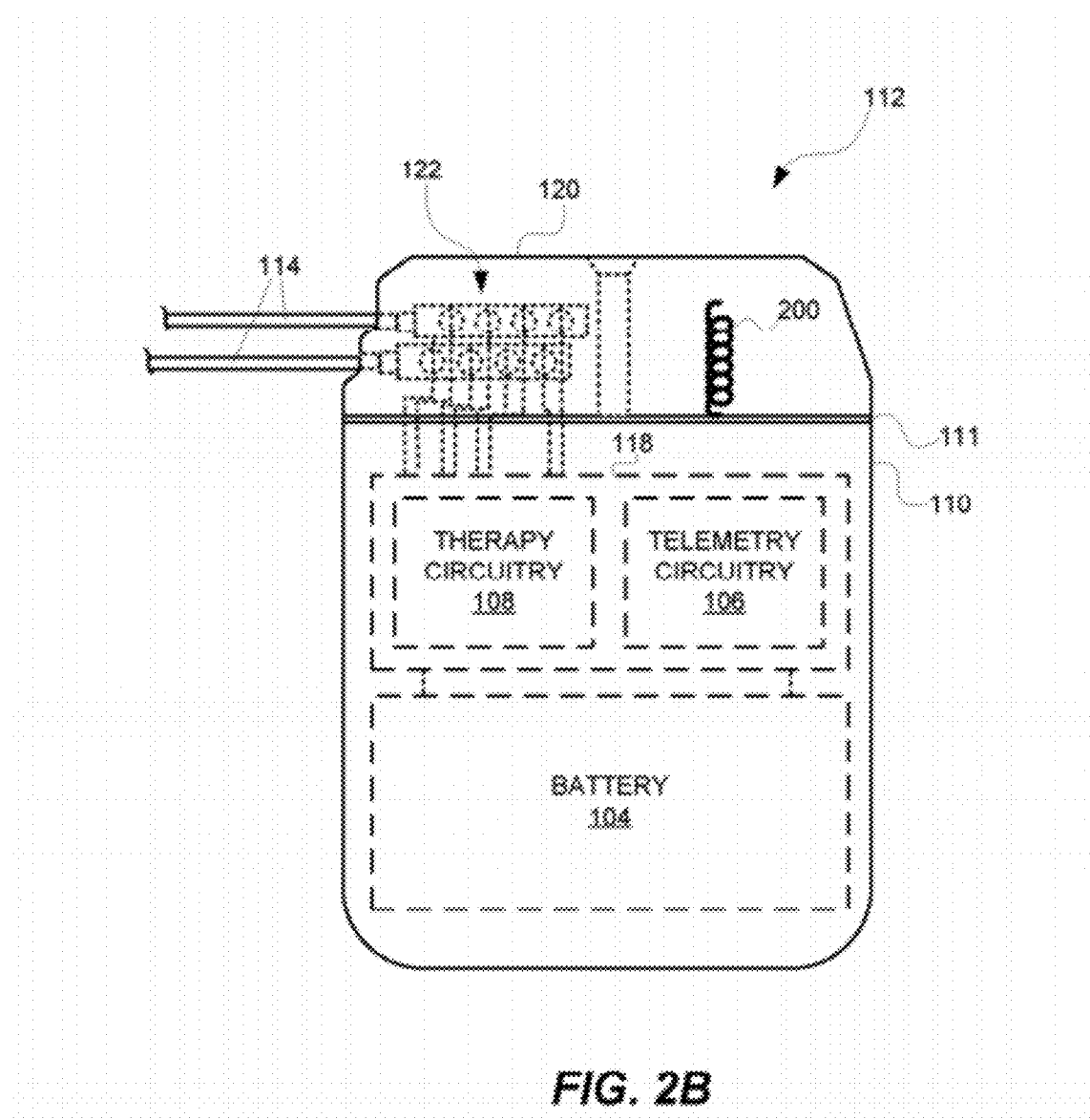
Figure 2C:
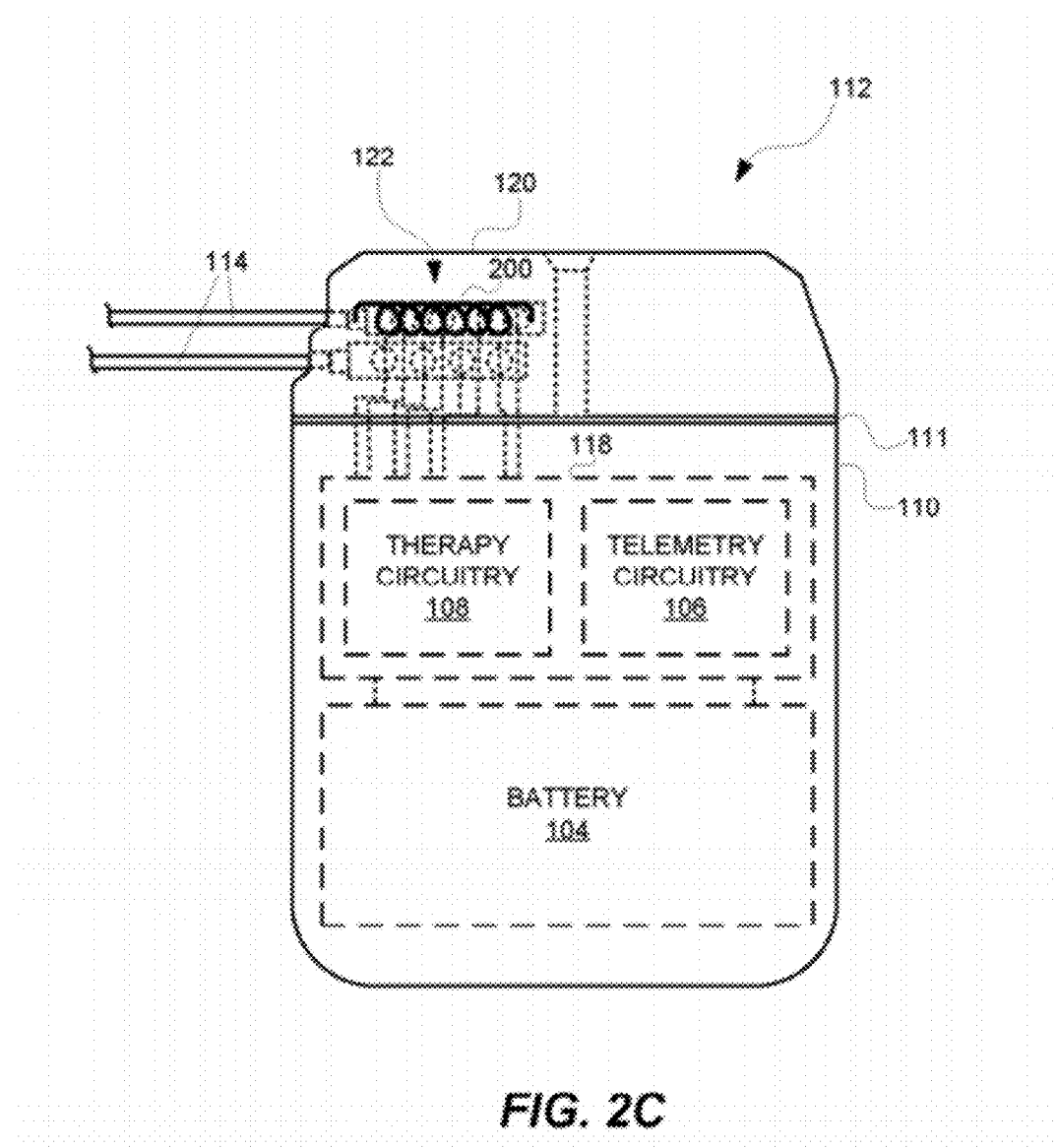

The following description is of various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

Figures 3A, 3B, 3C, 4:
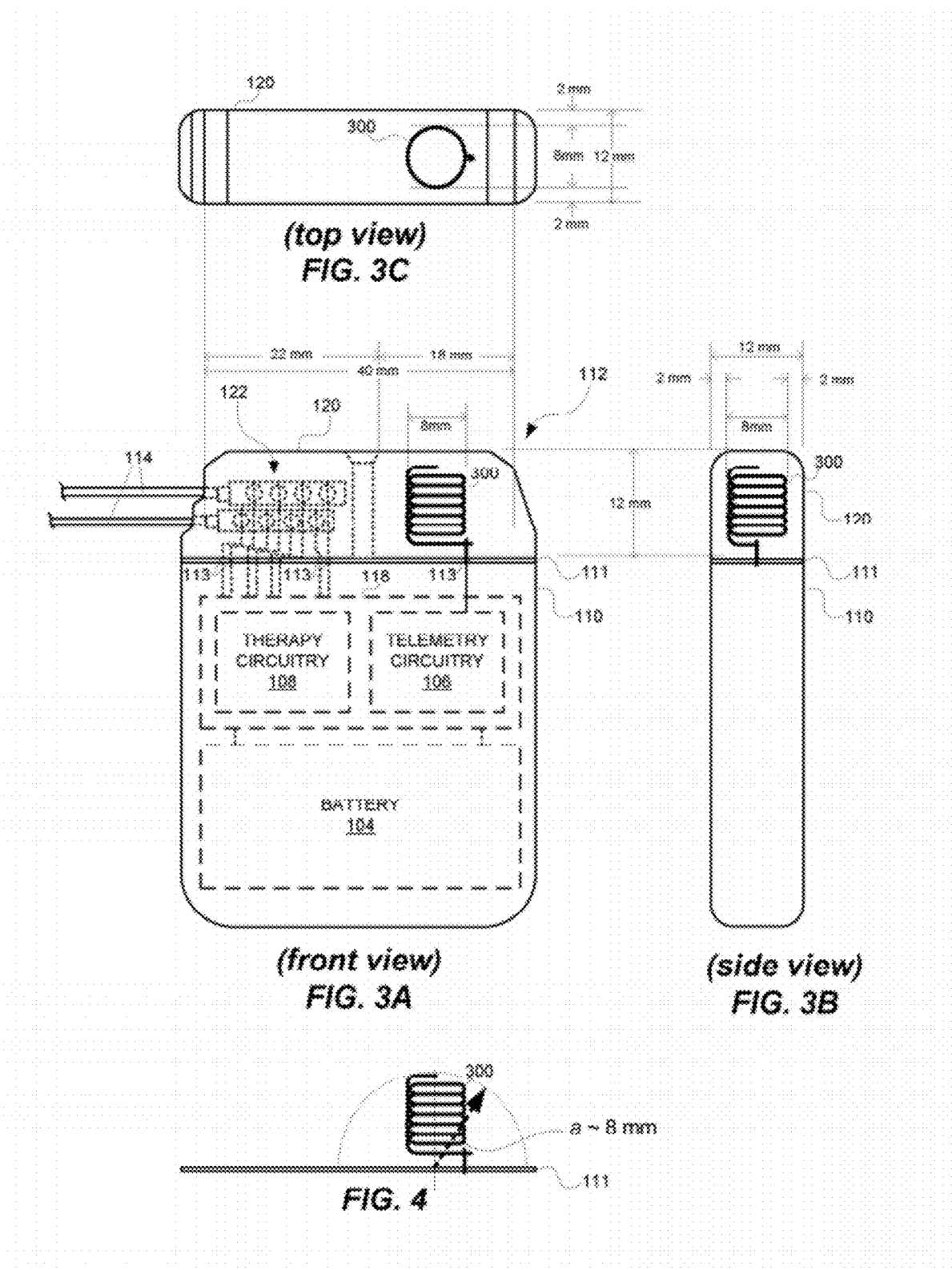
FIGS. 3A, 3B and 3C illustrate, respectively, a front view, side view and top view of an IMD including an antenna according to an embodiment of the present invention.
FIG. 4 illustrates how to draw a radius a of a sphere enclosing the maximum dimension of the antenna shown in FIGS. 3A-3C.

Exemplary dimensions of an IMD 112 are shown in FIGS. 3A-3C, with FIG. 3A illustrating a front view of the IMD, FIG. 3B illustrating a side view of the IMD, and FIG. 3C illustrating a top view of the IMD 112. The IMD includes a device housing 110 and a header 120. The device housing 110 can be made from a medical grade metal. The header 120 can be molded from a relatively hard, dielectric, non-conductive polymer or other plastic and has a thickness approximating the thickness of the device housing 110. As can be appreciated from FIGS. 3A-3C, the width of the IMD 112 is significantly greater than the thickness (i.e., depth) of the IMD 112. More specifically, the exemplary width is 40 mm, and the exemplary thickness is 12 mm. The header 120 includes a mounting surface that conforms to and is mechanically affixed to a mating sidewall surface 111 of the device housing 110. Assuming that the minimal thickness a wall of the header 120 is ~2 mm (in order to maintain the structural integrity of the header), this leaves only about 8 mm in thickness for embedding an antenna in the header 120. This would mean that if an antenna 300 were to be a true helical antenna, i.e., shaped as a true helix, the diameter of the helical antenna 300 would be limited to about 8 mm, as shown in FIGS. 3B and 3C. The overall circumferential shape of a true helical antenna is that of a right circular cylinder, as can be appreciated from FIGS. 3A-3C.

An antenna, such as the helical antenna 300, is an electrically small antenna (ESA). An electrically small antenna was defined by Harold Wheeler in 1947 as one whose maximum dimension is less than $\lambda/2\pi$. As explained in a paper by Randy Bancroft entitled "Fundamental Dimension Limits of Antennas" Centurion Wireless Technologies, Westminster, Colo., USA, pp. 1-14 (date unknown), this relation is often expressed as: k*a<1, where k=$2\pi/\lambda$, $\lambda$=free space wavelength (meters)

a=radius of a sphere enclosing the maximum dimension of the antenna (meters).

The free space wavelength $\lambda$=v/f; where v is the phase speed (magnitude of the phase velocity) of the wave and f is the wave's frequency. Assuming that the MICS/MedRadio frequency band is used for communication, which uses the RF band between 402 and 405 MHz, the center frequency of the MICS/MedRadio frequency range is 403.5 MHz. Accordingly, assuming v=3*10^8, and f=403.5*10^6, then $\lambda$=3*10^8/403.5*10^6=0.74 meters (0.74 meters=74 cm=740 mm). Thus, for a 403.5 MHz carrier signal, which corresponds to a wavelength of 74 cm, a half-wavelength dipole antenna would optimally be approximately 37 cm (i.e., 370 mm) long, and a quarter-wavelength monopole antenna would optimally have a length of approximately 18.5 cm (i.e., 185 mm) with the housing serving as a ground plane.

Referring to FIGS. 3A-3C, a straight wire antenna having a length of 370 mm or 185 mm would clearly not fit within the header 120. However, such lengths can potentially be achieved by forming the antenna as a helical antenna.

Where $\lambda$=0.74 meters, k=$2\pi/(0.74)$=8.49. As mentioned above, for an electrically small antenna, k*a<1. Accordingly, so long as a<1/(8.49), the antenna is an electrically small antenna. In other words, so long a is less than 0.118 meters (i.e., less than 118 mm), then the antenna is an electrically small antenna. As can be seen from FIG. 4, for the antenna 300, a ~8 mm. Thus, k*a=0.74*8*10^-3=0.006, which is less than 1. Accordingly, the antenna 300 is an electrically small antenna. The above analysis is performed in air with dielectric constant=1. The wavelength is reduced by 1/(dielectric constant)². The same analysis holds true for tissue with higher dielectric constants like skin, fat or muscle. The relation k*a<1 is not a hard limit for the concept that greater volume=greater gain and greater bandwidth. One could argue that the closer (larger) the antenna is to a monopole size, the better. The equations for electrically small antenna enable simple equation analysis for small antenna, regardless of shape, to demonstrate that larger volume improves antenna gain (G) and antenna bandwidth (BW), which are key performance parameters, as explained below.

The lower the antenna gain (G), the lower the available signal levels for RF communication and therefore the shorter the range of RF communication. The lower the antenna bandwidth (BW) the more sensitive an antenna is to variations in its environment. Conversely, the higher the antenna G the higher the available signal levels for RF communication, and therefore the longer the range of RF communication. Additionally, the higher the antenna BW the less sensitive an antenna is to variations in its environment. Accordingly, for a medical device, such as an IMD, both antenna BW and antenna G are preferably maximized to enable signals to be more readily received by the antenna of the medical device. Antenna BW is directly proportional to a. Additionally, antenna G is directly proportional to a. Thus, to maximize antenna BW and antenna G, it is desirable for a to be as large as possible, given the real-estate (i.e., portion) of the header that is available for placement of the antenna. Additionally, there are radiation pattern related benefits to having the antenna being three dimensional, as opposed to being flat (i.e., two dimensional).

In accordance with a first embodiment of the present invention, the telemetry antenna 300 is a true helical antenna having a maximum diameter possible for given a header's depth and a desired thickness of walls of the header 120. For example, the desired thickness of walls of the header 120 can be the minimal thickness that maintains the structural integrity of the header, but is not limited thereto. The electrically conductive housing 110 acts as the ground plane for the antenna 300, with the mating surface 111 being the closest surface of the ground plane to the antenna 300.

The antenna 300 is distinguishable from the helical antenna disclosed in the '065 patent, because the diameter of the helical antenna in the '065 patent appears very small compared to the portion of the header not being used to connect to leads. Advantages of the antenna 300 over the antenna in the '065 patent are that a is increased to thereby increase antenna BW and antenna G. Additionally, this embodiment achieves the radiation pattern related benefits to having the antenna 300 being three dimensional.

Referring now to FIGS. 5A-5C, in accordance with a second embodiment of the present invention, an electrically small telemetry antenna 500 resembles a helical antenna in that the antenna loops (also referred to as spirals) about a central axis 502 to form a three dimensional antenna. However, in this embodiment the telemetry antenna 500 is not a helical antenna, because antenna 500 does not have a cylindrical overall circumferential shape. Rather, in accordance with this second embodiment, the overall circumferential shape of the telemetry antenna 500 is generally that of a rectangular cuboid, as can be appreciated from FIGS. 5A-5C. A rectangular cuboid has six sides, with opposing sides (e.g., top and bottom, left and right, and back and front) being of the same size, and the overall shape being that of a rectangular six sided box. The sides of the rectangular cuboid shaped telemetry antenna 500 will most likely not meet at perfect right angles, but will rather likely be rounded, as can be appreciated from FIG. 5C. Referring to FIG. 5C, a longitudinal diameter 504 and a lateral diameter 506 of the rectangular cuboid shaped antenna 500 cross one another at the central axis 502, with the longitudinal diameter 504 being greater than the lateral diameter 506. The electrically conductive housing 110 acts as the ground plane for the antenna 500, with the mating surface 111 being the closest surface of the ground plane to the antenna 500.

Advantages of the antenna 500 (having the overall circumferential shape of a rectangular cuboid) over the antenna 300 (having the overall circumferential shape of a right circular cylinder) are that the antenna 500 has a greater antenna BW and a greater antenna G, as can be appreciated from FIG. 6. This is because a (the radius of a sphere enclosing the maximum dimension of the antenna) for the antenna 500 is greater than a for the antenna 300, as can be appreciated by comparing FIG. 6 to FIG. 4. In other words, the antenna 500 takes more advantage of the available space within the header 120 than the antenna 300. By increasing the radius a, the volume that the antenna 500 occupies increases, which is part of the reason that the BW and G increase. In FIG. 4, the exemplary value for the radius a is 8 mm, where in FIG. 6 the exemplary value for the radius a is 13.2 mm. The volume of a hemisphere can be calculated using the equation Volume=(2/3)*π*(r^3). Where r in the equation equals the radius a, the volume of a hemisphere corresponding to the antenna 500 of FIG. 6 is about 4,813 mm^3, which is over four times the 1,074 mm^3 volume of a hemisphere corresponding to the antenna 300 of FIG. 4.

Figure 7A:
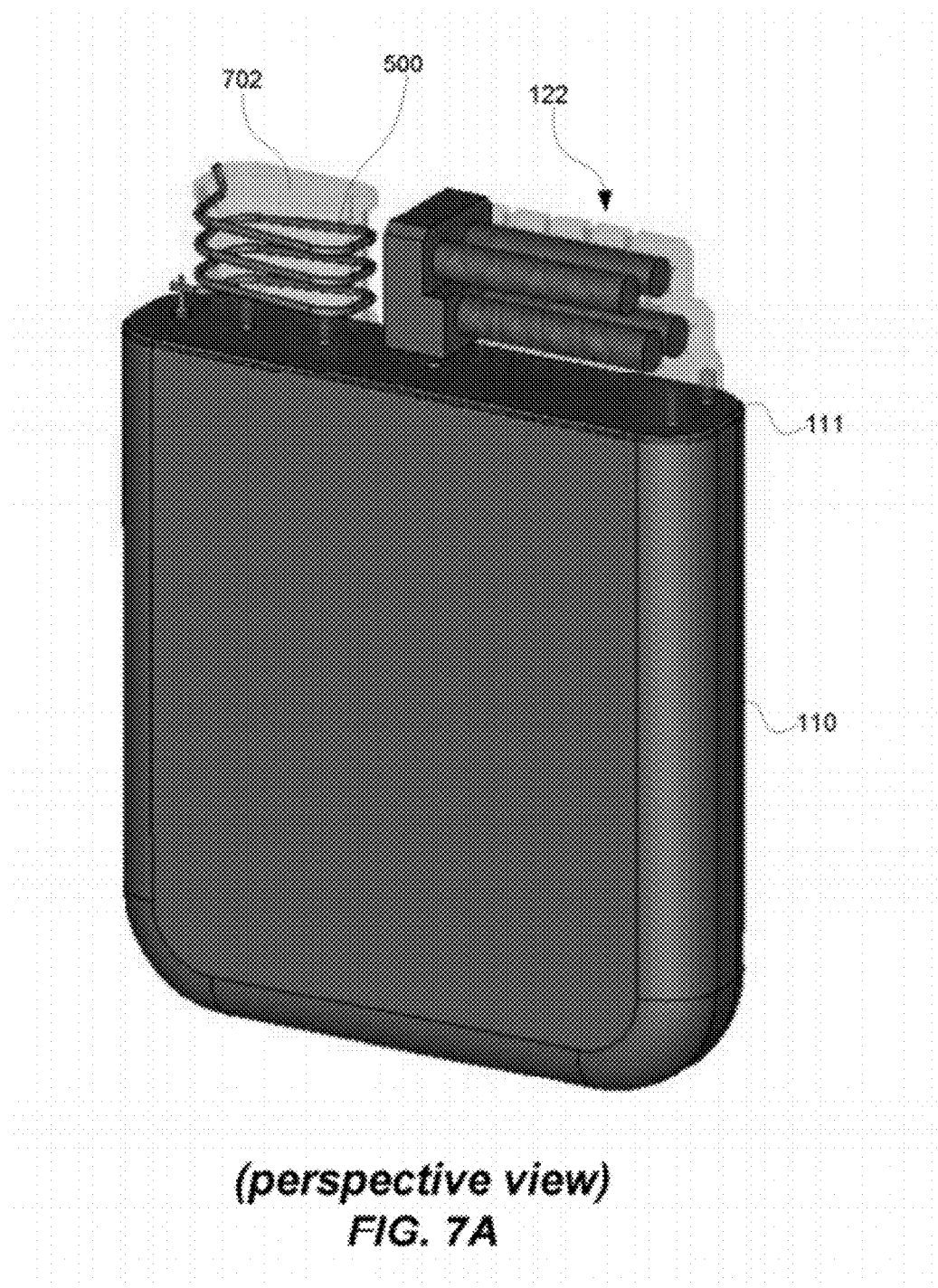
FIG. 7A illustrates a perspective view of a specific implementation of the antenna of the embodiment introduced in FIGS. 5A-5C.

FIG. 7A illustrates a perspective view of a specific implementation of the antenna 500 of the embodiment introduced in FIGS. 5A, 5B and 5C, with a portion of the header 120 removed. FIGS. 7B, 7C and 7D illustrate, respectively, a front view, a side view and a top view of the antenna 500 whose perspective view is shown in FIG. 7A. In accordance with an embodiment, the telemetry antenna 500 can be formed by winding a conductive wire at an angle around a generally rectangular cuboidal shaped central bobbin 702 so that the antenna generally has a rectangular cuboidal shape with a longitudinal length (i.e., the longitudinal diameter), a lateral width (i.e., the lateral diameter), and a height. The central bobbin 702, which can also be referred to as the spindle 702, is preferably made of a nonconductive dielectric material. For example, the spindle 702 can be made from the same dielectric, non-conductive polymer or other plastic that the header 120 is made from, but that need not be the case.

As explained above, by taking more advantage of the available space within the header 120 than the antenna 200, the antenna 300 achieves greater antenna G and antenna BW than the antenna 200. As also explained above, the antenna 500, by taking even more advantage of the available space within the header 112 than the antenna 300, achieves greater antenna G and antenna BW than the antenna 300. More specifically, by having its longitudinal diameter 504 greater than its lateral diameter 506, and having a rectangular cross section as opposed to a circular cross section, the antenna 500 occupies more volume than the antenna 300. In a further embodiment, illustrated with reference to FIGS. 8A, 8B and 8C, the overall circumferential shape of the antenna 800 is that of a square cuboid, which is a special type of rectangular cuboid where the longitudinal diameter 804 and the lateral diameter 806 are equal. The antenna 800 spirals about a central axis 802 to form a three dimensional antenna, with the longitudinal diameter 804 and the lateral diameter 806 crossing one another along the central axis 802. The antenna 800 will not provide as much antenna G and antenna BW as the antenna 500, but will have a greater antenna G and antenna BW than the antenna 300 having the right circular cylinder circumferential shape. This is in part because the volume of a square cuboid is greater than the volume of a right circular cylinder, assuming longitudinal and lateral diameters of the square cuboid are the same as the diameter of the right circular cylinder. The telemetry antenna 800 can be formed by winding a conductive wire at an angle around a generally square cuboid shaped central bobbin so that the antenna generally has a square cuboid shape with a longitudinal length (i.e., the longitudinal diameter), a lateral width (i.e., the lateral diameter), and a height, where the longitudinal diameter and lateral diameter are equal.

In still a further embodiment, illustrated with reference to FIGS. 9A, 9B and 9C, the overall circumferential shape of the antenna 900 is that of an elliptic or oval cylinder, where the longitudinal diameter 904 is greater than the lateral diameter 906. The antenna 900 spirals about a central axis 902 to form a three dimensional antenna, with the longitudinal diameter 904 and the lateral diameter 906 crossing one another along the central axis 902. The antenna 900 will not provide as much antenna G and antenna BW as the antenna 500, but will have a greater antenna G and antenna BW than the antenna 300 having the right circular cylinder circumferential shape. This is in part because the volume of an elliptic or oval cylinder is greater than the volume of a right circular cylinder, assuming the lateral diameter of the elliptic or oval cylinder is equal to the diameter of the right circular cylinder, and the longitudinal diameter of the elliptic or oval cylinder is greater than its lateral diameter. The telemetry antenna 900 can be formed by winding a conductive wire at an angle around a generally elliptic or oval cylinder shaped central bobbin so that the antenna generally has an elliptic or oval cylinder shape with a longitudinal length (i.e., the longitudinal diameter), a lateral width (i.e., the lateral diameter), and a height, where the longitudinal diameter is greater than the lateral diameter.

Figure 10:
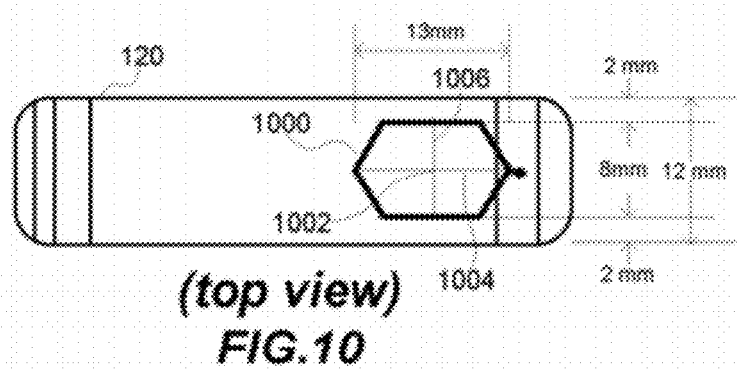
FIG. 10 illustrates a top view of an IMD including an antenna according to another embodiment of the present invention.
Figure 11:
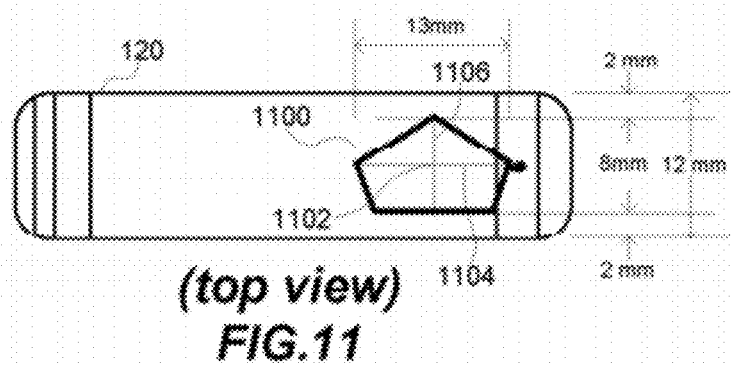
FIG. 11 illustrates a top view of an IMD including an antenna according to yet another embodiment of the present invention.

Further embodiments of the present invention encompass other three-dimensional shapes that could fit within the header 120 and have a larger volume than the helical antenna 300 having a right circular cylinder circumferential shape. For example, the top view of an antenna 1000 that is shaped like an elongated hexagonal prism is shown in FIG. 10, and the top view of an antenna 1100 that is shaped like an elongated pentagonal prism is shown in FIG. 11. These are just a few examples of other three-dimensional shapes that could fit within the header 120 and have a larger volume than the helical antenna 300 having a right circular cylinder circumferential shape. One of ordinary skill in the art reading this description will appreciate that additional shapes are possible and within the scope of the present invention, such as, but not limited to, an elongated heptagonal prism, an elongated octagonal prism, an elongated nonagonal prism, an elongated decagonal prism, an elongated hendecagonal prism, etc.

Referring to FIG. 10, the antenna 1000 has a longitudinal diameter 1004 that is greater than its lateral diameter 1006. The antenna 1000 spirals about a central axis 1002 to form a three dimensional antenna, with the longitudinal diameter 1004 and the lateral diameter 1006 crossing one another along the central axis 1002.

Referring to FIG. 11, the antenna 1100 has a longitudinal diameter 1104 that is greater than its lateral diameter 1106. The antenna 1100 spirals about a central axis 1102 to form a three dimensional antenna, with the longitudinal diameter 1104 and the lateral diameter 1106 crossing one another along the central axis 1102. However, it is noted that depending on the exact shape of the antenna, the antenna may not necessarily spiral about a central axis.

The antennas 1000 and 1100 will not provide as much antenna G and antenna BW as the antenna 500, but will have a greater antenna G and antenna BW than the antenna 300 having the right circular cylinder circumferential shape. This is in part because the volume of the elongated hexagonal prism and the volume of the elongated pentagonal prism are greater than the volume of a right circular cylinder, assuming the lateral diameter of the elongated hexagonal prism and the lateral diameter of the elongated pentagonal prism are equal to the diameter of the right circular cylinder, and the longitudinal diameter of the elongated hexagonal prism and the longitudinal diameter of the elongated pentagonal prism are greater than their lateral diameter.

The telemetry antennas 1000 and 1100 can be formed by winding a conductive wire at an angle around appropriately shaped central bobbins so that the antennas generally have, respectively, an elongated hexagonal prism shape and an elongated pentagonal prism shape, each with a longitudinal length (i.e., the longitudinal diameter), a lateral width (i.e., the lateral diameter), and a height, where the longitudinal diameter is greater than the lateral diameter.

Assuming that the MICS/MedRadio frequency band is used for communication, which has a center frequency of 403.5 MHz, this corresponds to λ=0.74 meters=74 cm=740 mm, as explained above. Accordingly, potential lengths for a wire used to form the antenna 300, 500, 800 or 900 (before the wire is spiraled to form the antenna 300, 500, 800 or 900) are approximately 370 mm (to provide a half-wavelength dipole antenna) and 185 mm (to provide a quarter-wavelength monopole antenna). Shorter lengths have also proved to provide satisfactory performance but at reduced gain and bandwidth.

An IMD is typically implanted under the skin within human body tissue in the upper buttock, abdomen or chest region. Human body tissue has higher dielectric properties (including a higher dielectric constant) than air. While the above discussions (including the theory and examples) of antenna G and antenna BW have assumed air dielectric properties, the same theory holds true for the higher dielectric properties found in human body tissue.

Exemplary Neurostimulation System

Figure 12:
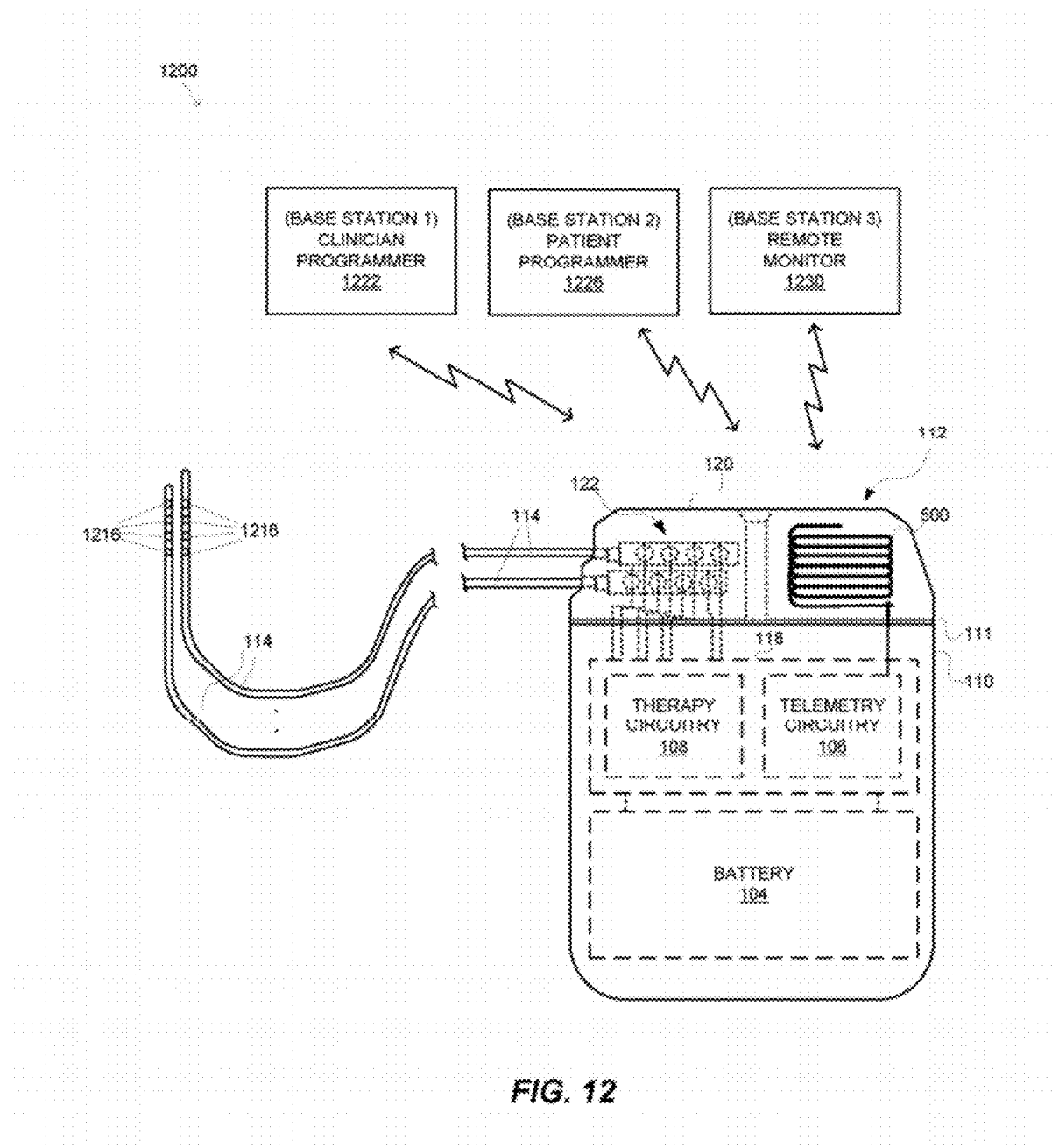
FIG. 12 illustrates an exemplary neurostimulation system with which an antenna of an embodiment of the present invention can be used.

The telemetry antennas, according to embodiments of the present invention described above, can be used by any type of IMD, including, but not limited to, an INS. To illustrate how the antennas can be included as part of an INS, an example neurostimulation system 1200 is illustrated in FIG. 12. The system 1200 includes an INS 112, which is typically implantable in a subcutaneous pocket within a patient's body. One or more leads 114 are connected to the header 120 of the INS 112, with each lead including one or more electrodes 1216. For example, four leads 114 can be connected to the INS 112, with each lead including four electrodes 116. Alternatively, more or less leads can be used, with more or less electrodes per lead. The INS 112 includes electronic circuitry 118 and a battery 104 within the housing 110. The electronic circuitry 118 includes therapy circuitry 108 and telemetry circuitry 106. Although not limited thereto, one or more leads 114 can be positioned so that the electrodes are disposed on or near a dorsal root ganglion (DRG). Additional details regarding such stimulation are provided in U.S. Pat. No. 7,450,993, entitled "Methods for Selective Stimulation of a Ganglion", and U.S. patent application Ser. No. 12/607,009, entitled "Selective Stimulation Systems and Signal Parameters for Medical Conditions", both of which are incorporated herein by reference.

The therapy circuitry 108 can be used to generate and provide an electrically stimulating signal (also referred to as a neurostimulation signal, a neurostimulation waveform, or simply a stimulation signal) to a nerve tissue via at least two of the electrodes 1216, with at least one of the electrodes connected as an anode, and at least one of the electrodes connected as a cathode. The telemetry circuitry 106 includes an RF transceiver for supporting RF communication or other wireless communication between the antenna 500 (or other antenna, e.g., 300, 800, 900, 1000 or 1100) of INS 112 and a non-implanted programmer or remote monitor. The programmer represented by block 1222, which is often referred to as a "clinician programmer", may be used by a representative of the INS manufacturer, a clinician, a physician and/or other medical personnel (collectively referred to hereafter as a "programming person"). Block 1226 represents another type of programmer, which is often referred to as a "patient programmer," which is primarily intended to be controlled by the patient within which the INS 112 is implanted. Block 1230 represents a remote monitor (e.g., a bedside monitor) that can at predetermined intervals, predetermined times, and/or in response to one or more triggering events, attempt to upload information from the INS 112. The programmer 1222 and/or 1226 can be used to program various stimulation parameters and/or other instructions into the electronic circuitry 118.

Neurostimulation parameter information can define how neurostimulation (also referred to simply as stimulation) is to be delivered using one or more leads 114. Such information can include lead selection information, electrode configuration information and stimulation waveform information. For example, such information can specify how each of the multiple electrodes (e.g., four electrodes) of each lead (e.g., four leads) is to be configured (i.e., as an anode electrode, a cathode electrode, or an inactive electrode), and can specify an amplitude, a pulse width and a pulse repetition rate of the stimulation waveform to be delivered using each lead.

In accordance with an embodiment, an external programmer (e.g., the clinician programmer 1222) wirelessly transmits neurostimulation parameter information data to the INS 112. More generally, data that is transmitted from an external programmer to the INS 112, which is used by the INS to generate and deliver neurostimulation signals, can be referred to as neurostimulation data. The INS can receive such neurostimulation data using its antenna 500 (or other antenna, e.g., 300, 800, 900, 1000 or 1100) and its telemetry circuitry 106. When appropriate, an external programmer (e.g., the clinician programmer 1222) can also wirelessly transmit a wake-up signal to the INS 112 over a different frequency band (e.g., an ISM band) than the frequency band (e.g., a MICS/RadioMed band) used to transmit neurostimulation data. The same antenna of the INS can be used to receive neurostimulation data as well as a wake-up signal, simultaneously, or at different times.

When the INS 112 receives neurostimulation data from the external programmer, the INS 112 can store the data in a portion of memory, such as, but not limited to, in non-volatile memory (e.g., flash).

Figure 13:
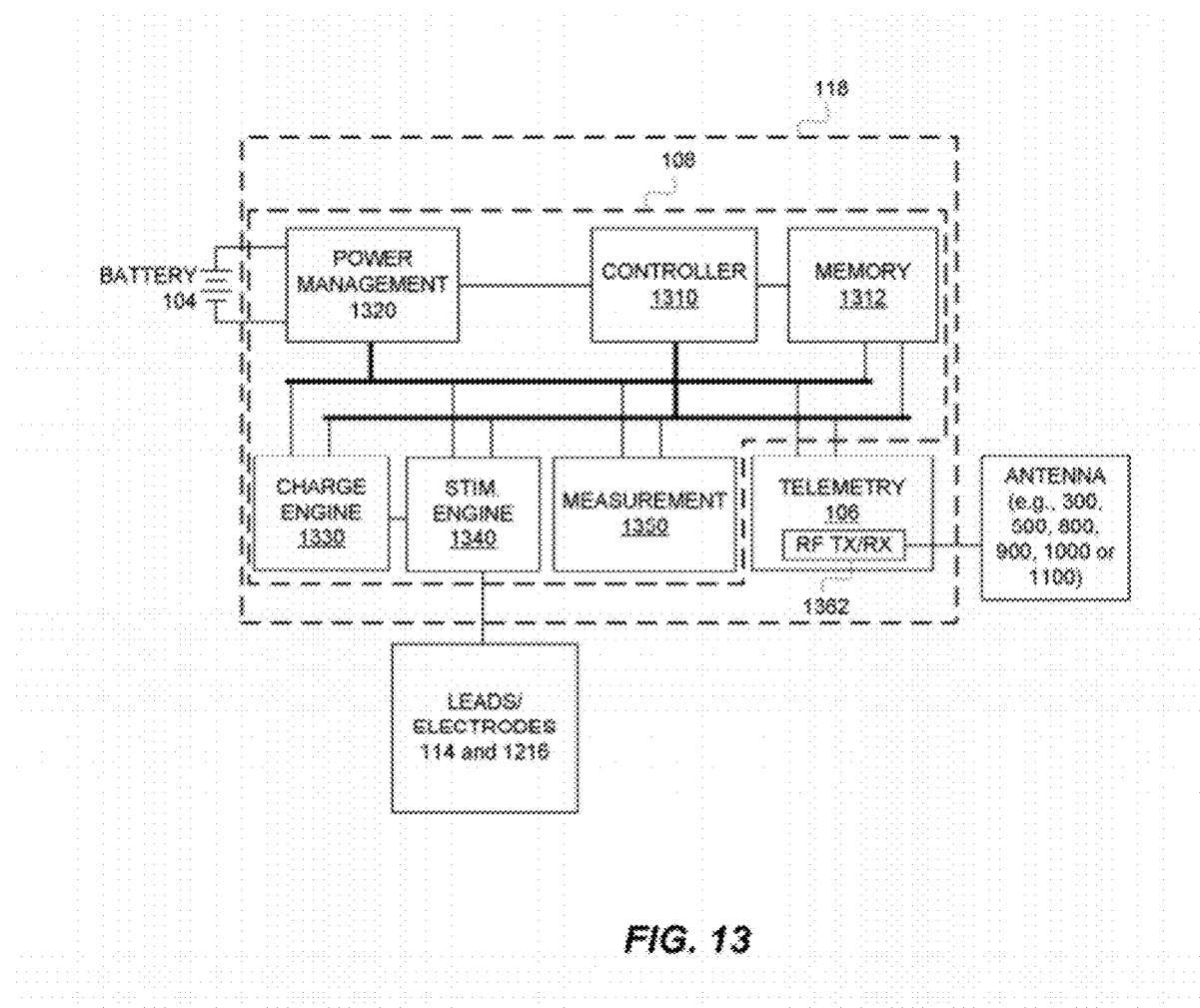
FIG. 13 illustrates exemplary details of the electronic circuitry of an implantable neurostimulator that can include an antenna according to an embodiment of the present invention.

FIG. 13 will now be used to describe exemplary details of the electronic circuitry 118 of the INS 112. Referring to FIG. 13, the therapy circuitry 108 is shown as including a controller 1310, memory 1312, power management circuitry 1320, charge engine circuitry 1330, stimulation engine circuitry 1340, measurement circuitry 1350. The controller 1310 can include a microprocessor, a microcontroller, a digital signal processor (DSP), an application specific integrated circuit (ASIC), a field-programmable gate array (FPGA), a state machine, or similar discrete and/or integrated logic circuitry. In a specific embodiment, the controller 1310 is implemented using a microcontroller unit (MCU), which can include one or more processors. A microcontroller or DSP can similarly include one or more processors.

The memory 1312 can include volatile and/or non-volatile memory including, but not limited to, RAM, ROM, NVRAM, EEPROM, flash memory, and the like. The memory 1312 can store neurostimulation data which can include electrode configuration information and stimulation waveform information.

The power management circuitry 1320 is shown as being connected to the battery 104, and is used to generate the appropriate voltage and/or current levels for powering the various other circuitry. Accordingly, the power management circuitry 1320 can include one or more DC-DC converters, such as, but not limited to, boost and/or buck converts. Additionally, or alternatively, the power management circuitry 1320 can include other types of voltage generators. The power management circuitry 1320 can also monitor the remaining battery life of the battery 104, so that a patient and/or medical personnel can be informed when the battery 104 needs to be replaced, or possibly recharged.

While not shown in FIG. 13, the therapy circuitry 108 can include control capacitors that store charges used to maintain, adjust and/or otherwise control charges stored by therapy output capacitors, wherein the therapy output capacitors are used to deliver stimulation to patient tissue. The charge engine circuitry 1330 can include and be used to charge up such control capacitors. The charge engine circuitry 1330 can also be used to sample the voltages stored on the therapy storage capacitors to make sure the appropriate charges are maintained and/or changed as necessary.

The stimulation engine circuitry 1340 is shown as being electrically connected to one or more leads 114, wherein each lead includes at least two electrodes 1216. The stimulation engine 1340 can include switches that are used to select specific leads and configure electrodes of selected leads as an anode, a cathode or as an inactive electrode.

The measurement circuitry 1350 can be used, e.g., to measure lead impedance, lead output current, lead output voltage, battery voltage and battery current, but is not limited thereto.

The telemetry circuitry 106 can include a radio frequency (RF) transceiver 1362 electrically connected to an antenna (e.g., 300, 500, 800, 900, 1000 or 1100) by a coaxial cable or other transmission line. The RF transceiver 1362 can include any well known circuitry for transmitting and receiving RF signals via the antenna to and from an RF transceiver of a non-implanted device, such as a clinician programmer, a patient programmer and/or a remote monitoring unit (e.g., 1222, 1226 and/or 1230). Such transceivers are available from various companies, such as, but not limited to, Zarlink Semiconductor Inc., headquartered in Ottawa, Canada.

In general, the electronic circuitry 118 can be used to communicate with a non-implanted BS, generate neurostimulation signals, and control switches to couple stimulation energy to selected electrodes of a selected lead. The stimulation pulses can be generated in accordance with parameters specified by neurostimulation data stored within the memory 1312. Exemplary programmable parameters that can be specified include the pulse amplitude, pulse width, and pulse repetition rate (also known as pulse frequency) for a neurostimulation waveform (also known as a neurostimulation signal), as was mentioned above.

While the antennas 300, 500, 800, 900, 1000 and 1100 have been described as being part of an INS, they can alternatively be part of other types of implantable devices, including, but not limited to, an implantable cardioverter defibrillator and/or pacemaker, and an implantable drug pump. In further embodiments the antennas 300, 500, 800, 900, 1000 and 1100 can be part of non-implanted medical devices, such as, but not limited to, a non-implanted ambulatory hemodynamic monitor that a patient carries around (e.g., in a pocket or attached to a belt). For another example, the MD can be a non-implanted neurostimulator device that replicates some or all of an INS's functions and can be connected to the patient to evaluate the efficacy of the proposed neurostimulation therapy. Such a non-implanted device is often referred to as a trial neurostimulator (TNS) device. The TNS device can be taped to a patient's back, hooked on a patient's belt, or attached to the patient in some other manner. It is also possible that a non-implanted neurostimulator device, similar to a TNS, can be used for extended periods of time, in which case the non-implanted device may no longer qualify as a "trial" device. When using such a TNS or other non-implanted neurostimulator device, stimulation lead(s) that extend from a non-implanted housing or header of the device can be inserted into the patient (e.g., percutaneously) so that distal portions of the lead(s) are positioned at appropriate locations, e.g., along the spinal cord. It is also possible that a non-implanted MD can be used for some other type of therapy besides neurostimulation. Where the MD is a non-implanted MD, the Wireless Medical Telemetry Service (WMTS) standard, which was defined by the FCC, can be used. However, embodiments of the invention are not limited to use of the WMTS communication standard. These are just a few examples, which are not meant to be limiting.

Embodiments of the present invention have been described above with the aid of functional building blocks illustrating the performance of specified functions and relationships thereof The boundaries of these functional building blocks have sometimes been defined herein for the convenience of the description. Alternate boundaries can be defined so long as the specified functions and relationships thereof are appropriately performed. Any such alternate boundaries are thus within the scope and spirit of the claimed invention.

Although the foregoing invention has been described in some detail by way of illustration and example, for purposes of clarity and understanding, it will be obvious that various alternatives, modifications and equivalents may be used and the above description should not be taken as limiting in scope of the invention.

What is claimed is:

1. A medical device, comprising:
a housing including a mating surface having a feed-through opening;
telemetry circuitry within the housing;
a header mechanically affixed to the mating surface of the housing;
one or more connectors within the header that is/are configured to receive a proximal end of one or more leads; and
an antenna within the header;
wherein the antenna is electrically connected to the telemetry circuitry within the housing;
wherein the antenna spirals about a central axis and has a rectangular cuboid circumferential shape; and
wherein the central axis, about which the antenna spirals, is perpendicular to the mating surface of the housing.

2. The medical device of claim 1, further comprising:
therapy circuitry, within the housing, electrically connected to the one or more connectors within the header;
wherein the therapy circuitry is configured to control stimulation that is deliverable via electrodes of one or more leads connected to the one or more connectors.

3. The medical device of claim 1, wherein:
a longitudinal diameter and a lateral diameter of the antenna, which are perpendicular to one another, cross one another at the central axis; and
the longitudinal diameter is greater than the lateral diameter;
the central axis about which the antenna spirals, which is perpendicular to the mating surface, is also perpendicular to each of the longitudinal diameter of the antenna and the lateral diameter of the antenna.

4. The medical device of claim 1, wherein:
a longitudinal diameter and a lateral diameter of the antenna cross one another at the central axis; and
the longitudinal diameter is substantially equal to the lateral diameter.

5. The medical device of claim 4, wherein the housing is electrically conductive and acts as a ground plane for the antenna, with the mating surface of the housing being a portion of the ground plane that is closest to the antenna.

6. The medical device of claim 1, wherein an antenna gain and an antenna bandwidth of the antenna having the rectangular cuboid circumferential shape are greater than an antenna gain and an antenna bandwidth of a helical antenna having a right circular cylinder circumferential shape that could fit within the header.

7. The medical device of claim 1, wherein a volume occupied by the antenna having the rectangular cuboid circumferential shape is greater than a volume that could be occupied by a helical antenna having a right circular cylinder circumferential shape that could fit within the header.

8. The medical device of claim 1, wherein the antenna is wound about a spindle having a rectangular cuboid shape.

9. The medical device of claim 8, wherein the rectangular cuboid shaped spindle includes six sides, wherein adjacent sides meet one another to form edges, and wherein at least some of the edges are curved.

10. The medical device of claim 9, wherein the antenna is formed by an electrically conductive wire that is wound about the spindle.

11. The medical device of claim 10, wherein the wire that forms the antenna includes straight portions and curved portions.

12. The medical device of claim 1, wherein the medical device is implantable.

13. The medical device of claim 12, wherein the medical device comprises an implantable neurostimulator.

14. A medical device, comprising:
a housing including a mating surface having a feed-through opening;
telemetry circuitry within the housing;
a header mechanically affixed to the mating surface of the housing;
one or more connectors within the header that is/are configured to receive a proximal end of one or more leads; and
an antenna within the header;
wherein the antenna is electrically connected to the telemetry circuitry within the housing;
wherein the antenna spirals about a central axis to form a three-dimensional shape including a longitudinal diameter, a lateral diameter and a height; and
wherein the longitudinal diameter of the antenna is greater than the lateral diameter of the antenna; and
wherein the central axis, about which the antenna spirals, is perpendicular to the mating surface of the housing, perpendicular to the longitudinal diameter of the antenna, perpendicular to the lateral diameter of the antenna, and parallel to the height of the antenna.

15. The medical device of claim 14, wherein the three-dimensional shape of the antenna comprises a rectangular cuboid.

16. The medical device of claim 14, wherein the three-dimensional shape of the antenna is selected from the group consisting of:
an elliptic cylinder;
an oval cylinder;
an elongated pentagonal prism;
an elongated hexagonal prism;
an elongated heptagonal prism;
an elongated octagonal prism;
an elongated nonagonal prism;
an elongated decagonal prism; and
an elongated hendecagonal prism.

17. The medical device of claim 14, wherein at least a portion of the housing is electrically conductive and acts as a ground plane for the antenna.

18. The medical device of claim 14, wherein the medical device is implantable.

19. The medical device of claim 18, wherein the medical device comprises an implantable neurostimulator.

20. An antenna for a medical device, comprising:
an electrically conductive wire that spirals to form a three-dimensional shape of a rectangular cuboid.

21. The antenna of claim 20, wherein a longitudinal diameter of the rectangular cuboid is greater than a lateral diameter of the rectangular cuboid.

22. The antenna of claim 20, wherein a longitudinal diameter of the rectangular cuboid is substantially equal to a lateral diameter of the rectangular cuboid.

23. The antenna of claim 20, wherein the antenna is sized to fit within a portion of a header of an implantable medical device.

24. An antenna for a medical device, comprising:
an electrically conductive wire that spirals to form a three-dimensional shape including a longitudinal diameter, a lateral diameter and a height;
wherein the longitudinal diameter of the antenna is greater than the lateral diameter of the antenna;
wherein the antenna includes a first end and a second end;
wherein the first end of the antenna is electrically connected to circuitry within a housing of the medical device by a conductor that extends from the first end of the antenna through a feed-through opening in the housing; and
wherein the second end of the antenna is a free end.

25. The antenna of claim 24, wherein the three-dimensional shape of the antenna comprises a rectangular cuboid.

26. The antenna of claim 24, wherein the three-dimensional shape of the antenna is selected from the group consisting of:
an elliptic cylinder;
an oval cylinder;
an elongated pentagonal prism;
an elongated hexagonal prism;
an elongated heptagonal prism;
an elongated octagonal prism;
an elongated nonagonal prism;
an elongated decagonal prism; and
an elongated hendecagonal prism.

27. The antenna of claim 24, wherein the antenna is sized to fit within a portion of a header of an implantable medical device.

28. The medical device of claim 1, wherein:
the antenna includes a first end and a second end;
the first end of the antenna is electrically connected to the telemetry circuitry by a conductor that extends from the first end of the antenna through the feed-through opening in the mating surface of the housing; and
the second end of the antenna is a free end.

29. The medical device of claim 1, wherein the free end of the antenna is located a distance from the mating surface of the housing, the distance being approximately equal to a height of the antenna.

30. The medical device of claim 14, wherein:
the antenna includes a first end and a second end;
the first end of the antenna is electrically connected to the telemetry circuitry by a conductor that extends from the first end of the antenna through the feed-through opening in the mating surface of the housing; and
the second end of the antenna is a free end.

31. The medical device of claim 30, wherein the free end of the antenna is located a distance from the mating surface, the distance being approximately equal to the height of the antenna.

32. The antenna of claim 24, wherein:
   the antenna spirals about a central axis to form the three-dimensional shape including the longitudinal diameter, the lateral diameter and the height; and
   the central axis is perpendicular to a surface of the housing having the feed-through opening.

* * * * *